United States Patent [19]

Eoga

[11] 4,362,639
[45] Dec. 7, 1982

[54] CLEANSER WITH IMPROVED AFTERODOR AND TARNISH RESISTANCE

[75] Inventor: Anthony B. J. Eoga, Boonton, N.J.

[73] Assignee: Warner-Lambert Company, Morris Plains, N.J.

[21] Appl. No.: 297,892

[22] Filed: Aug. 31, 1981

Related U.S. Application Data

[63] Continuation-in-part of Ser. No. 251,030, Apr. 3, 1981.

[51] Int. Cl.³ .............. C11D 3/395; C11D 7/10; C11D 7/18; C11D 17/00
[52] U.S. Cl. .............................. 252/99; 252/95; 252/98; 252/102; 252/174; 252/186.22; 252/186.38; 252/186.43; 252/387; 252/DIG. 16
[58] Field of Search ............ 252/95, 99, 102, 174, 252/98, 117, 186.22, 186.27, 186.32, 186.43, 387, 523, 541, DIG. 16, 186.38

[56] References Cited

U.S. PATENT DOCUMENTS

| | | | |
|---|---|---|---|
| 2,801,978 | 8/1957 | Perlman | 252/523 |
| 3,099,625 | 7/1963 | Gagliardi | 252/98 |
| 3,354,092 | 11/1967 | Perry | 252/111 |
| 3,458,446 | 7/1969 | Diaz | 252/99 |
| 3,558,497 | 1/1971 | Lawes | 252/99 |
| 3,704,227 | 11/1972 | Hill | 252/95 |
| 3,811,833 | 5/1974 | Statler | 252/102 |
| 3,893,954 | 7/1975 | Tivin | 252/548 |
| 3,996,151 | 12/1976 | Kirner | 252/186 |
| 4,028,263 | 6/1977 | Gray | 252/99 |
| 4,092,258 | 5/1978 | McLaughlin | 252/99 |
| 4,123,376 | 10/1978 | Gray | 252/99 |
| 4,295,985 | 10/1981 | Petrow | 252/105 |

*Primary Examiner*—Dennis L. Albrecht
*Attorney, Agent, or Firm*—Gary M. Nath; Stephen I. Miller

[57] ABSTRACT

A cleansing composition is disclosed comprising at least one oxidizing agent including an alkali monopersulfate salt, in an amount of from 35% to 60% by weight, a bleaching promotor selected from alkali metal and alkaline earth metal halides in up to about 20% by weight, a perborate salt in an amount sufficient to inhibit metal tarnish and corrosion and a compound providing ammonium ion in an amount effective to inhibit emission by the composition of chlorine-like odor or flavor. The composition forms a solution having a pH in the basic range.

Solutions containing the present cleaning composition exhibit improved tarnish and corrosion resistance, particularly in the instance where the solutions are used to clean dental appliances having metal parts.

57 Claims, No Drawings

CLEANSER WITH IMPROVED AFTERODOR AND TARNISH RESISTANCE

CROSS REFERENCE TO RELATED APPLICATIONS

The present application is a continuation-in-part of my copending Application Ser. No. 251,030, filed Apr. 3, 1981.

BACKGROUND OF THE INVENTION

1. Field of the Invention

The present invention relates generally to cleansers, and more particularly to those cleansers that include oxidizing and bleaching agents.

2. Description of the Prior Art

Cleanser compositions have for some time utilized oxidizing agents and bleaching agents in combination to remove visible stains from hard surfaces, and to remove scale or plaque buildup on those surfaces. Cleaning compositions, including those compositions containing abrasive materials for use as scouring cleansers, have employed a variety of sulfate salts as detergents, oxidizers and the like, and have utilized alkali metal and alkaline earth metal halides as bleaches.

U.S. Pat. No. 3,458,446 to Diaz discloses an abrasive cleaning composition that utilizes certain monopersulfate oxidizing agents in combination with a water-soluble bromide salt, in place of the chloride-liberating constituents conventionally used in such compositions. The patentee theorized that the replacement of the chloride constituents by the bromide constituents would eliminate the unpleasant odor of chlorine. The composition disclosed by Diaz was primarily intended for use in powdered form, and utilized a variety of additives, such as detergents, builders and the like, in its formulation.

In my earlier application identified above, I disclosed that a cleansing composition containing an oxidizing agent and a bleaching promoter may include a compound selected from alkali metal and alkaline earth metal perborates, for the purpose of promoting the effervescence of the composition, in the instance where such composition is utilized in static solution cleaning applications.

In addition to the problems addressed by my earlier application, certain other characteristics of static cleansing solutions, such as those utilized for dipping, soaking and the like have been noted. Specifically, despite the disclosure of Diaz, compositions utilizing some quantity of chloride salts therein tend to emit undesirable chlorine-like odor. In the instance where the cleansers were utilized for denture soaking solutions, both the undesirable odor and an equally undesirable aftertaste were experienced by the denture wearer.

A further problem has been noted in the instance where the solutions are utilized for soaking of articles having metallic surfaces. The metal surfaces of the soaked articles tend to tarnish or corrode in contact with the chloride and peroxygen bleaching agents, particularly when these agents are present in high concentrations, as they are in such compositions. This problem is particularly acute in the instance where the cleansers were utilized for soaking dentures, as the dental alloys such as the cobalt-chromium alloys, vitallium, and the like were adversely effected and easily tarnished.

A need therefore exists for the preparation of a cleanser that addresses both of the foregoing drawbacks by reducing or eliminating unwanted chlorine odor and aftertaste, as well as the corrosion and tarnish that occurs when the cleansers are utilized with various metals and their alloys.

SUMMARY OF THE INVENTION

In accordance with the present invention, a cleansing composition is prepared which includes at least one oxidizing agent including an alkali metal monopersulfate salt, present in amounts ranging from about 35 to about 60% by weight, a bleaching promoter selected from the group consisting of alkali metal and alkaline earth metal halides, present in an amount of up to about 20%, a perborate salt present in an amount sufficient to inhibit the tarnish and corrosion of metals in contact with the composition, and a compound providing ammonium ion present in amounts effective to inhibit the emission by the composition of chlorine-like odor or flavor. The composition forms a solution having a pH in the basic range, and may include sodium carbonate in amounts ranging from 20-40% and sodium hydroxide in amounts of up to 0.5%, to assist in pH maintenance.

Preferably, the oxidizing agent may comprise potassium monopersulfate, and may be present in an amount ranging from about 40% to about 50% by weight. Sodium chloride may comprise the bleaching promoter, and may be present in an amount ranging from 10% to 20% by weight, the perborate salt may be selected from alkali metal and alkaline earth metal perborates, and may be present in amounts of at least 7% by weight, and preferably from about 7% to about 20% by weight, and the ammonium ion-providing compound may be present from about 0.09% to about 6% by weight.

Solutions containing the present cleansing composition exhibit improved tarnish and corrosion resistance, particularly valuable in the instance where the solutions are utilized to clean dental appliances having metal parts. Also, the compositions are found to effectively inhibit tarnish and corrosion at a wide range of temperatures.

The present compositions also inhibit the evolution of chlorine-like odors and flavors, so that, in the instance where the present compositions are used to form a solution for cleaning dentures, neither of the undesirable effluents is present.

The present cleansing compositions may also contain various additives, such as colorants, perfumes, and the like. The present compositions may be prepared in tablet form, and may accordingly also include tableting agents, excipients, disintegrants and the like. In this latter form, the cleansing compositions may be formulated to serve as either denture cleansers, or toilet bowl cleansers.

Accordingly, it is a principal object of the present invention to prepare cleansing compositions offering tarnish and corrosion resistance over a wide temperature range.

It is a further object of the present invention to provide cleansing compositions capable of inhibiting the evolution of chlorine-like odor and flavor when said compositions are placed in solution.

It is a yet further object of the present invention to prepare cleansing compositions as aforesaid which are particularly useful as denture cleansers.

Other objects and advantages will become apparent to those skilled in the art from a consideration of the ensuing description

DETAILED DESCRIPTION

The cleansing compositions of the present invention comprise an oxidizing agent that may be selected from alkali metal and alkaline earth metal monopersulfate salts, and preferably alkali metal monopersulfate salts. The oxidizing agent may be present in amounts ranging from about 35% to about 60%, and preferably 40% to 50% by weight. The alkali metal monopersulfate salts are preferably the potassium or sodium salts, which are commercially available. The potassium salt is preferred, and may, if desired, be employed in the form of a triple salt with potassium bisulfate and potassium sulfate, e.g., $KHSO_5.KHSO_4.K_2SO_4$.

In the mole ratio of about 2:1:1, the foregoing triple salt is known commercially by the trademark "OX-ONE®" and is sold by E. I. duPont DeNemours & Co., Inc.

The bleaching promoter or component is likewise well known, and may be selected from the group consisting of alkali metal and alkaline earth metal halides, in amounts ranging up to 20%, and preferably from 10% to 20% by weight of the composition. The halide salt is preferably selected from alkali metal halides such as the sodium and potassium salts. In a preferred embodiment, sodium chloride is utilized in an amount ranging between 10% and 20% by weight of the composition.

The ability of the compositions of the present invention to inhibit the evolution of the undesirable chlorine-like odor or aftertaste, when the compositions are disposed in solution, is due to the presence of one or more compounds that provide effective amounts of ammonium ion. In particular, these compounds are selected from the group consisting of ammonium chloride, ammonium sulfate, ammonium citrate, ammonium phosphate and mixtures thereof, and are present in amounts ranging from about 0.09% to about 6% by weight of the composition, these percentages based upon monovalent ammonium ion. In particular, ammonium chloride, ammonium sulfate and ammonium citrate are particularly effective odor and taste inhibiters. Ammonium citrate may be utilized alone in amounts ranging from about 0.6% to about 6% by weight; alternately, ammonium citrate may be present in combination with ammonium sulfate in ratios with respect to each other that may range from about 2:1 to about 3:1.

More particularly, the compound providing ammonium ion may be present in amounts ranging from about 0.4% to about 3% by weight, and most particularly from about 1.1% to about 2.2% by weight. The aforementioned ammonium compounds have been found to provide yet further advantages, in that they contribute to the improved tarnish and corrosion resistance of the present compositions. Particularly, ammonium citrate is most notable, both alone, or in combination with ammonium sulfate as mentioned above, as it is capable of providing both odor and aftertaste inhibition and corrosion and tarnish resistance when utilized within the amounts set forth herein.

In addition to the ammonium ion-providing compounds, the present compositions include a perborate salt that advantageously cooperates with the ammonium ion-providing compounds to confer tarnish and corrosion resistance through a broad temperature range. In particular, the present compositions utilizing both the ammonium ion-providing compounds and the perborate salts within the ranges set forth herein, exhibit corrosion and tarnish resistance over a wide range of temperatures, including temperatures on the order of 20° C., as well as elevated temperatures. This broad spectrum of corrosion and tarnish resistance is particularly important, in the instance where the present compositions are utilized to form denture cleansers and toilet bowl cleansers, as the compositions are placed in solutions which are frequently maintained for extended periods of time at room temperature or below.

The perborate salts useful in the present invention comprise the alkali metal and alkaline earth metal perborates. Preferably, the perborate salts as selected from the alkali metal salts, such as sodium and potassium, and in a preferred embodiment, sodium perborate monohydrate is utilized. The perborate salts may be present in amounts of at least 7% by weight, and may range from 7% to 20% by weight, or more specifically, from 7% to about 10% by weight. In a preferred embodiment of the present invention, the perborate salts are utilized in amounts ranging from about 7.5% to about 8.5% by weight of the composition. As noted in my copending Application Serial No. the perborate salts favorably contribute to reduced chlorine-like odor and aftertaste evolution, as well as providing low temperature corrosion and tarnish resistance.

The corrosion and tarnish resistance of the present compositions is particularly notable when the compositions are placed in solution and utilized, for example, as denture cleansers. In such instance, dental alloys such as the cobalt-chromium alloys, and the like may be exposed to the solution for periods of time in excess of twelve hours, with no development of corrosion or tarnish. When the present compositions are prepared with ammonium chloride, for example, the combination of ammonium chloride with either citric acid or ammonium citrate, as well as other compounds known as sequestrants, such as the tetrasodium salt of ethylene diamine tetraacetic acid, and trisodium phosphate, favorably contributes to reduced corrosion and tarnish resistance. Naturally, the present compositions may be varied within the limits set forth above, to provide the improved properties of both corrosion and tarnish resistance, and reduced chlorine-like odor and aftertaste evolution.

As noted earlier, the cleansing compositions described above may be prepared in various formulations, and, accordingly, may contain certain additional ingredients selected on the basis of desired end use. Thus, for example, the compositions may include additional detergent compounds, including organic and inorganic detergents, including non-ionic detergents such as the various polyoxyethylene ethers of aromatic and aliphatic alcohols, as well as the polyoxyethylene ethers of hydrophobic propylene oxide polymers. These compounds assist in maintaining a foaming action, in the instance where the cleansing compositions are placed in aqueous solution.

Also, the compositions may contain other adjuvant materials, that may be inorganic or organic in structure. Thus, inorganic water-soluble alkaline builders such as alkali and alkaline earth metal carbonates, tetrapyrophosphates, tripolyphosphates, phosphates, metasilicates and hydroxides, and mixtures of these may be added. Particularly, sodium carbonate may be present in an amount ranging from 20 to 40%, and preferably in an amount of from 25 to 30%, as it functions not only as a builder, but enhances effervescence and assists in stabilizing the pH of the solutions obtained from the composition. In this latter capacity, sodium hydroxide may be added to assist in pH stabilization and may be present in amounts of up to about 0.5%, and preferably 0.3% to 0.5%.

The present compositions may also contain sequestrants for the purpose of maintaining solution clarity, in the instance where the compositions are placed in solution. Also, as mentioned earlier, the sequestrants may assist in the inhibition of corrosion and tarnish. Sequestrants useful in the present invention include ethylene diamine tetraacetic acid (EDTA) and its corresponding alkali salts, as well as other polyfunctional organic acids, such as citric acid, maleic acid, and their corresponding salts. The sequestrants may be present in amounts of up to about 3.5%, and preferably 0.3% to 3.5% by weight of the composition.

In the instance where the composition is to be prepared for use as a denture cleanser, other additives such as flavorings, colorants, perfumes and the like may be added in various amounts, as mentioned earlier. For example, the flavorings may include varieties of mint, oil of clove, artificial vanilla flavoring, and others. These materials may be included and blended in various combinations within the scope of the present invention. The choice of the required amounts is likewise within the skill of the art.

In the instance where the present cleansing compositions are formulated for use as denture cleansers, the colorants useful herein are those known as F.D. & C. and D. & C. dyes and lakes. These materials are certified by the Federal Food and Drug Administration as acceptable for use in food, drug and and cosmetic applications, and drug and cosmetic colorings. The materials acceptable for the foregoing spectrum of use are preferably water-soluble, and include indigoid dye, known as F.D. & C. Blue No. 2, which is the disodium salt of 5,5'-indigotindisulfonic acid. Similarly, the dye known as F.D. & C. Green No. 1, comprises a triphenylmethane dye and is the monosodium salt of 4-[4-(N-ethyl-p-sulfobenzylamino)diphenylmethylene]-[1-(N-ethyl-N-p-sulfoniumbenzyl)-$\Delta^{2,5}$-cyclohexadienimine]. A full recitation of all F.D. & C and D. & C. and their corresponding chemical structures may be found in the Kirk-Othmer Encyclopedia of Chemical Technology, at Volume 5, pages 857–884, which text is accordingly incorporated herein by reference. Dyes and colorants will fade at different rates and may be chosen to provide specific end points.

The foregoing colorants may be blended with each other in a variety of combinations. It is particularly desirable that the colorants be chosen so that the composition when initially dissolved will present a deep hue. This is important in the instance where the composition serves as a denture cleanser, as the fading phenomenon embodied in denture cleansers can be more easily observed by the end user.

In accordance with a further embodiment of the invention, the present cleansing compositions may be prepared to include a fade control agent, in the instance where the compositions contain a colorant such as previously described, and are to be utilized in applications where cessation of composition activity is signified by disappearance of the color. The fade control agent may comprise a compound providing soluble halide ion, as disclosed in my copending application Ser. No. 251,030, the entire disclosure of which is incorporated herein by reference.

The compositions of the present invention are capable of preparation by a variety of techniques, depending upon the intended end use. In the instance where the present compositions are to serve as denture cleansers, it is desirable to prepare the compositions in tablet form. The use of the present compositions in tablet form is commercially preferred, as it is easier to achieve the uniformity of quantity and distribution of the ingredients of the compositions that is necessary to assure the corresponding uniformity of performance of the denture cleanser. Thus, cleanser tablets have been found to exhibit uniformity of color reaction, disintegration and fade time, and cleaning ability on a tablet-to-tablet basis.

To enable the present composition to be prepared in tablet form, certain ingredients, including excipients, tableting agents and the like are added, and the resulting composition is then compressed to form the final tablet. The particular tableting additives utilized herein comprise conventional materials normally utilized for such purpose, and may be selected and employed in amounts determined within the skill of the art.

In the instance where the contemplated composition is to contain a halide such as sodium chloride, it is advisable to add the basic component such as sodium carbonate, to the ingredients prior to adding the monopersulfate salt, in order to avoid undue or premature reactivity of the resulting mixture.

A fuller understanding of the present invention will be gained from a review of the following illustrative examples. Unless specified otherwise, all amounts expressed as percent are deemed to be percent by weight of the total composition.

EXAMPLES 1–17

A series of cleanser compositions were prepared having the ingredients set forth in Table I, below.

The compositions were prepared in tablet form, each tablet weighing approximately 3.3 grams. Tablets from certain of the examples were thereafter immersed in approximately 125 milliliters of water, and a series of soaks of denture tiles and dental metals were performed to measure stain and plaque removal as well as tarnish resistance. The soaks were performed according to two regimes; both a series of five (5) twelve minute soaks, and extended soaks of from overnight to two days, i.e. 48 hours, were conducted. Also, the tests were performed at both 45° C. and 20° C. (room temperature).

TABLE I

| | INGREDIENTS | QUANTITIES, WEIGHT % EXAMPLE NO. | | | | | | | | |
|---|---|---|---|---|---|---|---|---|---|---|
| | | 1 | 2 | 3 | 4 | 5 | 6 | 7 | 8 | 9 |
| 1. | Sodium Chloride Fine Prepared | 13.8 | 13.8 | 13.8 | 13.8 | 10.6 | 10.6 | 11 | 11 | 11 |
| 2. | Ammonium Chloride | — | — | — | — | — | — | — | — | — |
| 3. | Ammonium Citrate | 1.3 | 1.3 | 1.3 | 1.3 | 1.3 | 1.3 | — | — | — |
| 4. | Ammonium Sulfate | .5 | .5 | .5 | .53 | .55 | .56 | — | — | — |
| 5. | Monoammonium Phosphate | — | — | — | — | — | — | 1.1 | 1.1 | 1.1 |
| 6. | Water, Potable USP | .19 | .19 | .19 | .19 | — | — | .46 | .46 | .46 |
| 7. | Sodium Carbonate Anhydrous Soda Ash Dense | 26.9 | 26.9 | 26.9 | 26.9 | 27.9 | 27.9 | 29.3 | 29.3 | 29.3 |
| 8. | Trisodium Phosphate, Anhydrous, Food Grade, | | | | | | | | | |

TABLE I-continued

| | | | | | | | | | | |
|---|---|---|---|---|---|---|---|---|---|---|
| | Granular | .85 | .85 | .85 | .85 | .88 | .88 | — | — | — |
| 9. | Potassium Monopersulfate Compound | 45.3 | 45.3 | 45.3 | 45.2 | 47 | 47 | 49.4 | 49.4 | 49.4 |
| 10. | Ethylenediaminetetraacetic Acid Tetrasodium Salt Dihydrate/Pure | .7 | .7 | .7 | .7 | .73 | .73 | .77 | .77 | .77 |
| 11. | Sodium Perborate Monohydrate | 5.7 | 7.1 | 8.5 | 8.5 | 8.8 | 8.8 | 6.2 | 6.2 | 6.2 |
| 12. | FD&C Blue Colors, mixed | — | — | — | .11 | .13 | .14 | .23 | .23 | .23 |
| 13. | Flavor and Fragrance | .87 | .87 | .87 | .87 | .91 | .91 | .95 | .95 | .95 |
| 14. | Detergent | .14 | .14 | .14 | .14 | .2 | .2 | .15 | .15 | .15 |
| 15. | Sodium Benzoate Special Powder | .53 | .53 | .53 | .45 | .47 | .47 | .49 | .49 | .49 |
| 16. | Magnesium Stearate USP | .06 | .06 | .06 | .12 | .13 | .13 | .14 | .14 | .14 |
| 17. | Polytetrafluoroethylene Powder | .34 | .34 | .34 | .34 | .35 | .35 | .24 | .24 | .24 |
| 18. | Erythorbic Acid | 2.8 | 1.4 | — | — | — | — | — | 1.5 | — |
| 19. | Sodium Erythorbate | — | — | — | — | — | — | 1.5 | — | — |
| 20. | Sodium Gluconate | — | — | — | — | — | — | — | — | 1.5 |

| | | QUANTITIES, WEIGHT % EXAMPLE NO. | | | | | | | |
|---|---|---|---|---|---|---|---|---|---|
| | INGREDIENTS | 10 | 11 | 12 | 13 | 14 | 15 | 16 | 17 |
| 1. | Sodium Chloride Fine Prepared | 11 | 11 | 14.2 | 13.8 | 10.9 | 10.8 | 10.7 | 10.6 |
| 2. | Ammonium Chloride | — | — | — | — | — | — | — | — |
| 3. | Ammonium Citrate | — | — | 1.3 | 1.28 | 1.37 | 1.35 | 1.33 | 1.32 |
| 4. | Ammonium Sulfate | — | — | .56 | .55 | .58 | .57 | .56 | .56 |
| 5. | Monoammonium Phosphate | 1.1 | 1.1 | — | — | — | — | — | — |
| 6. | Water, Potable USP | .46 | .46 | .17 | .17 | — | — | — | — |
| 7. | Sodium Carbonate Anhydrous Soda Ash Dense | 29.3 | 29.3 | 27.7 | 26.9 | 28.8 | 28.6 | 28.2 | 28 |
| 8. | Trisodium Phosphate, Anhydrous, Food Grade, Granular | — | — | .87 | .85 | .9 | .9 | .89 | .88 |
| 9. | Potassium Monopersulfate Compound | 49.4 | 49.4 | 46.7 | 45.3 | 48.5 | 48.2 | 47.5 | 47.1 |
| 10. | Ethylenediaminetetraacetic Acid Tetrasodium Salt Dihydrate/Pure | .77 | .77 | .73 | .71 | .75 | .75 | .74 | .74 |
| 11. | Sodium Perborate Monohydrate | 6.2 | 6.2 | 5.8 | 8.5 | 6.1 | 6.8 | 8.2 | 8.8 |
| 12. | FD&C Blue Colors, mixed | .23 | .23 | .2 | .2 | .16 | .16 | .16 | .16 |
| 13. | Flavor and Fragrance | .95 | .95 | .9 | .88 | .94 | .93 | .92 | .91 |
| 14. | Detergent | .15 | .15 | .15 | .14 | .18 | .18 | .18 | .18 |
| 15. | Sodium Benzoate Special Powder | .49 | .49 | .47 | .45 | .49 | .48 | .47 | .47 |
| 16. | Magnesium Stearate USP | .14 | .14 | .05 | .05 | .16 | .16 | .16 | .15 |
| 17. | Polytetrafluoroethylene Powder | .24 | .24 | .35 | .34 | .12 | .12 | .12 | .12 |
| 18. | Erythorbic Acid | — | — | — | — | — | — | — | — |
| 19. | Sodium Erythorbate | — | — | — | — | — | — | — | — |
| 20. | Gluconic Acid | 1.5 | — | — | — | — | — | — | — |

The compositions prepared in Table I all exhibited improved chlorine-like odor and aftertaste suppression, when materials soaked in the solutions prepared with the respective compositions were later examined. In the instance of dental metals exposed to the solutions in the manner outlined above, it was noted that the compositions in which the perborate salt was present in amounts less than 7%, yielded solutions that caused tarnishing, particularly at the lower temperature of 20° C. The results of the tarnish resistance testing conducted with the compositions of Examples 4–17, is set forth in Table II, below.

TABLE II

| | TARNISH RESISTANCE | | | |
|---|---|---|---|---|
| EXAMPLE NO. | OVER-NIGHT SOAK 45° C. | OVER-NIGHT SOAK 20° C. | 5 × 12 MIN. SOAKS 45° C. | 5 × 12 MIN. SOAKS 20° C. |
| 4 | C | C | C | C |
| 5 | C | C | C | C |
| 6 | C | C | C | C |
| 7 | — | — | C | SS |
| 8 | — | — | C | SS |
| 9 | — | — | S | S |
| 10 | — | — | S | S |
| 11 | — | — | S | S |
| 12 | C | S | S | C |
| 13 | C | C | C | C |
| 14 | C | S | C | S |
| 15 | C | SS | C | SS |
| 16 | C | C | C | C |
| 17 | C | C | C | C |

C = Clean or No Tarnish
S = Tarnished
SS = Slightly Tarnished

The foregoing compositions were also examined for pH and color fade, in the instance where colorants were included. The tablet samples gave good color reactions and fade times were within accepted ranges, i.e. no more than 17 minutes, and the pH of the respective tablets was in the basic range, and generally at a pH of 9 or above.

This invention may be embodied in other forms or carried out in other ways without departing from the spirit or essential characteristics thereof. The present invention is therefore to be considered as in all respects illustrative and not restrictive, the scope of the invention being indicated by the appended claims, and all changes which come within the meaning and range of equivalency are intended to be embraced therein.

What is claimed is:

1. A cleansing composition comprising:
  (a) an oxidizing agent containing a monopersulfate salt in an amount of from 35% to 60% by weight;

(b) a bleaching promoter selected from alkali metal and alkaline earth metal halides, in an amount up to about 20% by weight;
(c) a perborate salt present in amounts sufficient to inhibit tarnish and corrosion of metal; and
(d) a compound providing ammonium ion in an amount effective to inhibit evolution from said cleansing composition of chlorine-like odor and taste.

2. The composition of claim 1, wherein said perborate salt is selected from alkali metal and alkaline earth metal perborates and mixtures thereof.

3. The composition of claim 2, wherein said perborate salt comprises an alkali metal perborate.

4. The composition of claim 3, wherein said perborate salt comprises potassium perborate monohydrate.

5. The composition of any one of claims 1-3 or 4, wherein said perborate salt is present in amounts of at least 7% by weight.

6. The composition of claim 5, wherein said perborate salt is present in amounts ranging from about 7% to about 20% by weight.

7. The composition of claim 6, wherein said perborate salt is present in amounts ranging from about 7% to about 10% by weight.

8. The composition of claim 7, wherein said perborate salt is present in amounts ranging from about 7.5% to about 8.5% by weight.

9. The composition of claim 1, wherein said compound providing ammonium ion is present in an amount sufficient to provide from about 0.09% to about 6% of said ammonium ion, based upon the monovalent form thereof.

10. The composition of either claims 1 or 9, wherein said compound providing ammonium ion is selected from ammonium chloride, ammonium sulfate, ammonium citrate, ammonium phosphate and mixtures thereof.

11. The composition of claims 1 or 9, wherein said compound providing ammonium ion is present in amounts ranging from about 0.4% to about 3% by weight.

12. The composition of claim 10, wherein said compound providing ammonium ion is present in amounts ranging from about 0.4% to about 3% by weight.

13. The composition of claim 11, wherein said compound providing ammonium ion is present in amounts ranging from about 1.1% to about 2.2%.

14. The composition of claim 12, wherein said compound providing ammonium ion is present in amounts ranging from about 1.1% to about 2.2%.

15. The composition of claim 10, wherein said compound providing ammonium ion comprises ammonium chloride.

16. The composition of claim 10, wherein said compound providing ammonium ion comprises ammonium citrate.

17. The composition of claim 16, wherein said ammonium citrate is present in an amount ranging from about 0.6% to about 6% by weight.

18. The composition of claim 10, wherein said compound providing ammonium ion comprises a mixture of ammonium citrate and ammonium sulfate.

19. The composition of claim 18, wherein said ammonium citrate and said ammonium sulfate are present in a ratio with respect to each other of from about 2:1 to about 3:1.

20. The composition of claim 1, wherein said oxidizing agent comprises an alkali metal of monopersulfate salt.

21. The composition of claim 20, wherein said monopersulfate salt comprises potassium monopersulfate.

22. The composition of claims 1, 20 or 21, wherein said monopersulfate salt is present in an amount of from 40% to 50% by weight.

23. The composition of claim 1, wherein said bleaching promoter comprises an alkali metal halide.

24. The composition of claim 23, wherein said halide is selected from the group consisting of chloride, bromide, iodide and mixtures thereof.

25. The composition of claim 24, wherein said halide comprises chloride, and said bleaching promoter is sodium chloride.

26. The composition of claims 23, 24 or 25, wherein said bleaching promoter is present in an amount of from 10% to 20% by weight.

27. The composition of claim 1 further including at least one material selected from the group consisting of builders, sequestrants, detergents, colorants, perfumes, flavorings, excipients, pH stabilizers, tableting agents, disintegrants, and mixtures thereof.

28. The composition of claim 28, wherein said builders are selected from the group consisting of alkali metal carbonates, alkali metal phosphates, and mixtures thereof; said sequestrants comprise polyfunctional organic acids, and their alkali metal salts; said pH stabilizers comprise sodium hydroxide; and said colorants comprise at least one food, drug and cosmetic or drug and cosmetic grade dye or lake.

29. The composition of claim 29, wherein said builders are selected from sodium carbonate, trisodium phosphate, and mixtures thereof, in a total amount ranging from 20 to 40% by weight; said sequestrants comprise the alkali metal salts of ethylenediamine tetraacetic acid in an amount of from 0.3-3.5% by weight; and said colorants are selected from food, drug and cosmetic grade dyes or lakes having the individual colors blue, red and green, and mixtures thereof in amounts of up to about 0.5% by weight.

30. A cleansing composition comprising:
(a) an oxidizing agent comprising a monopersulfate salt in an amount of from 35% to 60% by weight;
(b) a bleaching promoter comprising an alkali metal halide in an amount of from 10% to 20% by weight;
(c) a perborate salt present in an amount of at least 7% by weight to inhibit tarnish and corrosion of metal; and
(d) a compound providing ammonium ion in an amount effective to inhibit evolution from said cleansing composition of chlorine-like odor and taste, said compound present in an amount sufficient to provide from about 0.09% to about 6% of said ammonium ion, based on its monovalent form.

31. The composition of claim 30, wherein said perborate salt is selected from alkali metal and alkaline earth metal perborates and mixtures thereof.

32. The composition of claim 31, wherein said perborate salt comprises an alkali metal perborate.

33. The composition of claim 32, wherein said perborate salt comprises potassium perborate monohydrate.

34. The composition of claims 30-32 or 33, wherein said perborate salt is present in amounts ranging from about 7% to about 20% by weight.

35. The composition of claim 34, wherein said perborate salt is present in amounts ranging from about 7% to about 10% by weight.

36. The composition of claim 35, wherein said perborate salt is present in amounts ranging from about 7.5% to about 8.5% by weight.

37. The composition of claim 30, wherein said compound providing ammonium ion is selected from ammonium chloride, ammonium sulfate, ammonium citrate, ammonium phosphate and mixtures thereof.

38. The composition of claim 37, wherein said compound providing ammonium ion comprises ammonium chloride.

39. The composition of claim 37, wherein said compound providing ammonium ion comprises ammonium chloride.

40. The composition of claim 39, wherein said ammonium citrate is present in an amount ranging from about 0.6% to about 6% by weight.

41. The composition of claim 37, wherein said compound providing ammonium ion comprises a mixture of ammonium citrate and ammonium sulfate.

42. The composition of claim 41, wherein said ammonium citrate and said ammonium sulfate are present in a ratio with respect to each other of from about 2:1 to about 3:1.

43. The composition of any one of claims 30, 37–39 or 41, wherein said compound providing ammonium ion is present in amounts ranging from about 0.4% to about 3% by weight.

44. The composition of claim 43, wherein said compound providing ammonium ion is present in amounts ranging from about 1.1% to about 2.2%.

45. A cleansing composition exhibiting improved tarnish resistance and reduced evolution of chlorine-like odor and taste when disposed in a solution, comprising:
(a) an oxidizing agent containing a monopersulfate salt in an amount of from 35% to 60% by weight;
(b) a bleaching promoter comprising an alkali metal halide in an amount ranging from 10% to 20% by weight;
(c) a perborate salt in an amount of from 7% to 20%, to inhibit tarnish and corrosion of metal; and
(d) a compound providing ammonium ion selected from the group consisting of ammonium chloride, ammonium sulfate, ammonium citrate, ammonium phosphate and mixtures thereof, said compound present in an amount sufficient to provide from about 0.09% to about 6% of said ammonium ion based on monovalent ammonium.

46. The composition of claim 45, wherein said perborate salt comprises an alkali metal perborate.

47. The composition of claim 46, wherein said perborate salt comprises potassium perborate monohydrate.

48. The composition of claims 45, 46 or 47, wherein said perborate salt is present in amounts ranging from about 7% to about 10% by weight.

49. The composition of claim 48, wherein said perborate salt is present in amounts ranging from about 7.5% to about 8.5% by weight.

50. The composition of claim 45, wherein said compound providing ammonium ion comprises ammonium chloride.

51. The composition of claim 45, wherein said compound providing ammonium ion comprises ammonium citrate.

52. The composition of claim 51, wherein said ammonium citrate is present in amount ranging from about 0.6% to about 6% by weight.

53. The composition of claim 45, wherein said compound providing ammonium ion comprises a mixture of ammonium citrate and ammonium sulfate.

54. The composition of claim 53, wherein said ammonium citrate and said ammonium sulfate are present in a ratio with respect to each other of from about 2:1 to about 3:1.

55. The composition of claims 45, 50, 51, 53 or 54, wherein said compound providing ammonium ion is present in amounts ranging from about 0.4% to about 3% by weight.

56. The composition of claim 55, wherein said compound providing ammonium ion is present in amounts ranging from about 1.1% to about 2.2% by weight.

57. A tablet useful as a denture cleanser comprising the composition of claims 1, 30 or 45.

* * * * *